United States Patent [19]
Dominguez et al.

[11] Patent Number: 5,476,108
[45] Date of Patent: Dec. 19, 1995

[54] METHOD AND APPARATUS FOR DETECTING FOREIGN MATTER WITHIN A LAYER OF TABACCO

[75] Inventors: Luis M. Dominguez, Winston-Salem; Sydney K. Seymour, Clemmons, both of N.C.

[73] Assignee: R. J. Reynolds Tobacco Company, Winston-Salem, N.C.

[21] Appl. No.: 927,551

[22] Filed: Aug. 6, 1992

Related U.S. Application Data

[63] Continuation of Ser. No. 505,192, Apr. 5, 1990, abandoned.
[51] Int. Cl.$^6$ .................................................. A24B 15/00
[52] U.S. Cl. ........................................... 131/108; 131/905
[58] Field of Search ..................................... 131/905–907, 131/84.1, 84.3, 84.4, 280, 108

[56] References Cited

U.S. PATENT DOCUMENTS

| | | |
|---|---|---|
| 3,980,882 | 9/1976 | Carr-Brion et al. . |
| 4,095,696 | 6/1978 | Sherwood . |
| 4,190,061 | 2/1980 | Heitmann et al. . |
| 4,204,950 | 5/1980 | Burford, Jr. . |
| 4,225,242 | 9/1980 | Lane . |
| 4,257,777 | 3/1981 | Dymond et al. . |
| 4,398,894 | 8/1983 | Yamamoto . |
| 4,533,252 | 8/1985 | Cahen et al. . |
| 4,595,027 | 6/1986 | Higgins et al. ...................... 131/906 X |
| 4,640,614 | 2/1987 | Roberts et al. . |
| 4,657,144 | 4/1987 | Martin et al. ...................... 131/905 X |
| 4,707,652 | 11/1987 | Lowitz . |
| 4,781,742 | 11/1988 | Hill et al. . |
| 4,839,602 | 6/1989 | Pletcher . |
| 4,860,772 | 8/1989 | Hensgen et al. ...................... 131/905 X |
| 4,865,052 | 9/1989 | Hartmann et al. ................... 131/905 X |
| 4,878,506 | 11/1989 | Pinck et al. ......................... 131/905 X |
| 4,885,709 | 12/1989 | Edgar et al. . |
| 4,893,253 | 1/1990 | Lodder . |
| 4,926,886 | 5/1990 | Lorenzen et al. .................... 131/905 X |
| 4,941,482 | 7/1990 | Heitmann et al. ................... 131/905 X |
| 4,971,077 | 11/1990 | Dominguez et al. ................ 131/905 X |

OTHER PUBLICATIONS

Isaac Landa, "Visible (VIS) Near Infra Red (NIR) Rapid Spectrometer For Laboratory and On Line Analysis of Chemical and Physical Properties"; SPIE vol. 665, Optical Techniques for Industrial Inspection, pp. 286–289 (1986).
"Food Processors Bet On On–Line NIR Analysis for Big Gains"; Food Engineering (Mar. 1988).
K. J. Rashmawi et al; "Near Infrared Analyzer Reveals Moisture In Minutes"; Chemical Processing, (Jun., 1988).
Robert A. Lodder et al; "Quantile BEAST Attacks the False–Sample Problem in Near–Infrared Reflectance Analysis"; Applied Spectroscopy, vol. 42, No. 8, 1988, pp. 1351–1365.
Robert A. Lodder et al.; "Detection of Subpopulations in Near–Infrared Reflectance Analysis"; Applied Spectroscopy, vol. 42, No. 8, 1988, pp. 1500–1511.
Howard L. Mark et al; "Qualitative Near–Infrared Reflectance Analysis Using Mahalanobis Distances"; Analytical Chemistry, vol. 57, No. 7, Jun. 1985, pp. 1449–1456.

Primary Examiner—Jennifer Bahr

[57] ABSTRACT

The invention is directed to a method and apparatus for detecting foreign matter including small particles of organic materials such as plastics within a layer of tobacco. The tobacco is irradiated with a plurality of selected NIR radiation wavelength bands. Data representative of the NIR radiation exiting the tobacco is compared to a predetermined reference representative of a plurality of different tobacco samples to determine whether the inspected tobacco contains foreign matter.

47 Claims, 6 Drawing Sheets

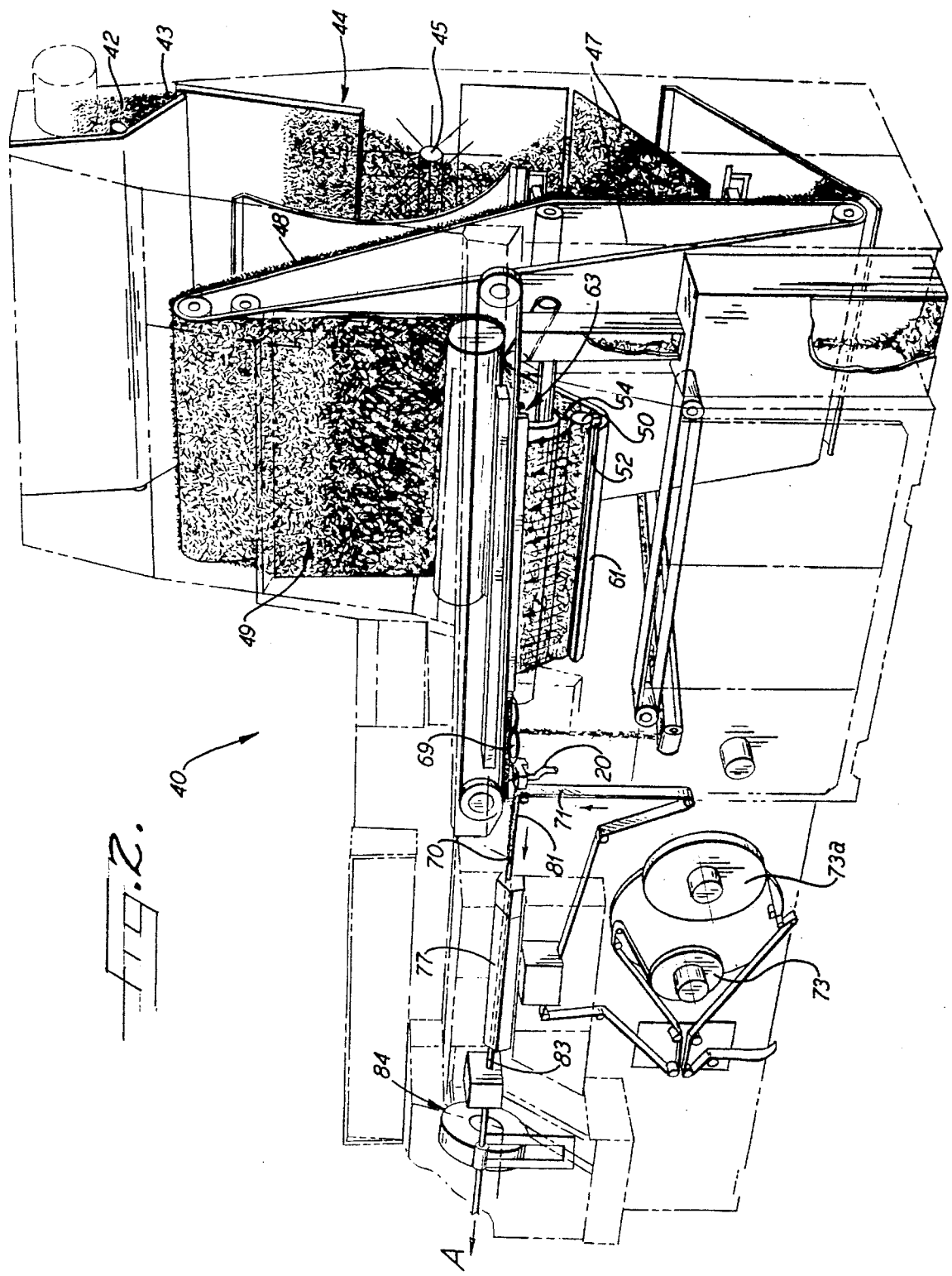

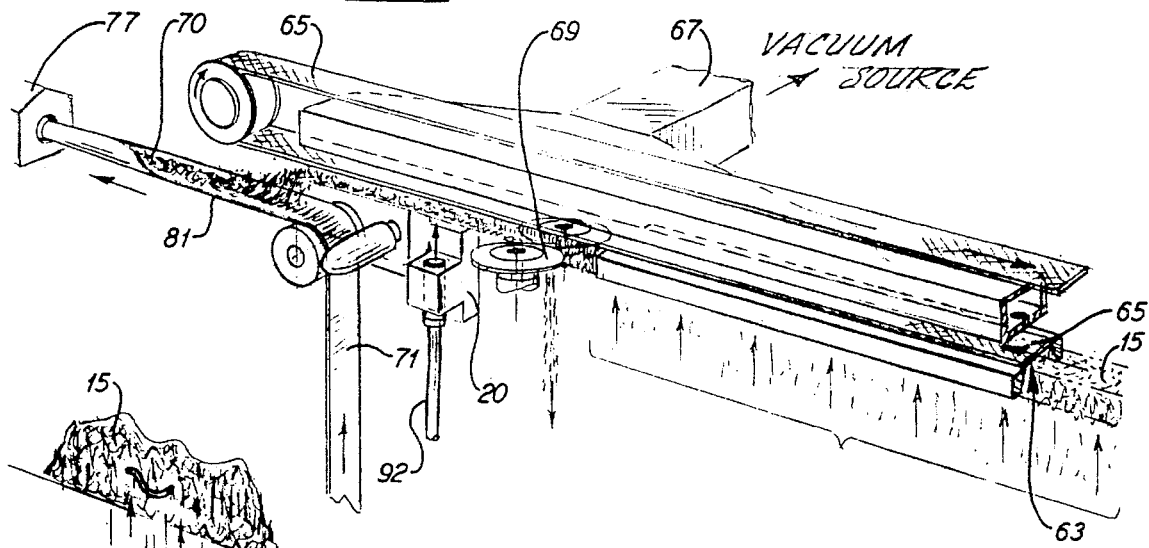
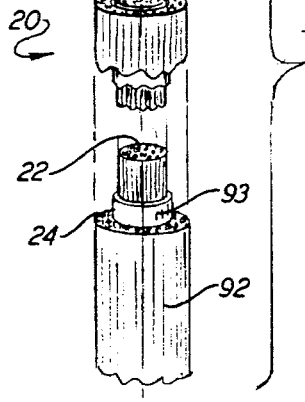
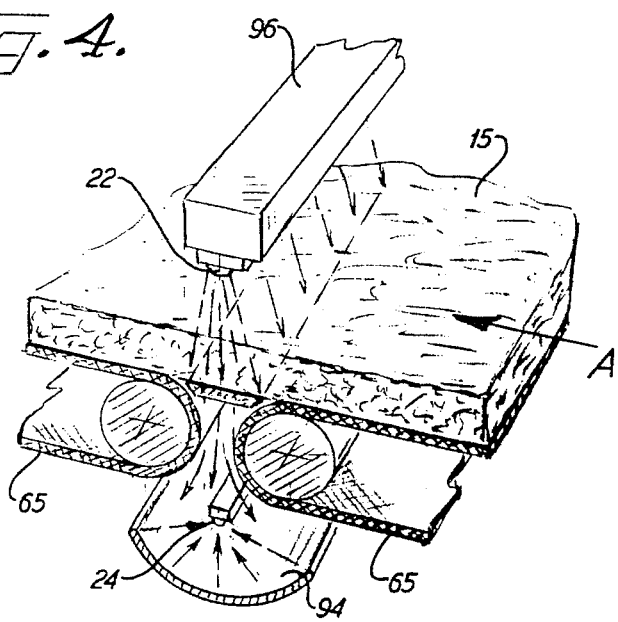

METHOD AND APPARATUS FOR DETECTING FOREIGN MATTER WITHIN A LAYER OF TABACCO

This is a continuation of application Ser. No. 07/505,192, filed Apr. 5, 1990, now abandoned.

FIELF OF THE INVENTION

The invention relates to a method and apparatus for inspecting a layer of tobacco.

BACKGROUND OF THE INVENTION

The manufacture of tobacco products such as cigarettes is a complicated process.

Typically, tobacco in the form of leaf is received from the farmer and passed to a determined operation in which large stems are removed to produce destemmed tobacco. The destemmed tobacco is packed into bales which are then stored for a suitable time period of up to several years. Following removal from storage, the tobacco bales are fed to a primary processing operation in which the tobacco is removed from the bale, cut into strips and treated to remoisturize the tobacco. Various types of tobacco strip including Burley, Flue Cured and Oriental tobaccos, are blended according to a predetermined recipe. The blended tobacco is then treated by adding various flavorants to provide a cased tobacco which is cut at 20–40 cuts per inch to provide tobacco "cut filler." Various other types of tobacco can be added to the cut filler including puffed tobacco, reconstituted tobacco, tobacco reclaimed from rejected cigarettes, and the like, to provide a final product blend. This blend is then fed to a continuous cigarette rod making apparatus.

During the processing and transport of tobacco filler to the rod-forming unit, certain undesirable impurities and matter foreign to the cigarette can come into contact therewith. The processing sequence therefore include numerous separation steps for the removal of undesirable material. Nevertheless, minute amounts of foreign matter such as pieces of string, plastic wrapping material, paper and the like can be inadvertently incorporated into the tobacco rods and the final cigarette product.

A variety of techniques have been suggested to monitor tobacco or provide quality control of tobacco for undesirable foreign matter. Quality control has usually been accomplished off-line by collecting samples from the factory floor and taking them to a remote site for analysis. The results usually are too late for any significant quality control to be effected. The more typical situation is that the product may be fully manufactured before results are available from the laboratory. Thus, an entire batch of cigarettes may have to be rejected to ensure that it does not have any undesirable impurities or foreign matter therein.

An on-line technique for monitoring tobacco has been suggested in U.S. Pat. No. 4,707,652 to Lowitz which discloses an impurity detector for tobacco utilizing scattered electromagnetic radiation. On or more detectors generate a signal indicating the intensity of the scattered intensity of a normal sample. A change in the output of the detector indicates the presence of an impurity. Such an apparatus is, however, bulky and can be influenced by various extraneous factors such as relative humidity in the manufacture environment, varying amounts of moisture in the tobacco and different types of tobacco in the tobacco blend.

Another on-line technique has been suggested in U.S. Pat. No. 4,839,602 to Pletcher which discloses a device for detecting metal particles in a stream of tobacco. Inductive changes caused by the presence of metal are detected by a detector. The detector generates a signal to the operator indicating the presence of a metallic object.

Other radiation techniques have been suggested for quality control of other difficult to analyze samples or products. U.S. Pat. No. 4,095,696 to Sherwood discloses a produce grader utilizing near infrared (hereinafter "NIR") reflectance technology to distinguish rocks and dirt among fruits and vegetables such as tomatoes or to sort tobacco leaves according to their colors.

The use of NIR reflectance has been suggested for use in quality control of pharmaceuticals for the detection of impurities by Mark et al in *Analytical Chemistry*, 1985, 57, pp 1449–1456 and in U.S. Pat. No. 4,893,253 to Ladder. Pharmaceuticals are extremely pure and typically have no more than 4 or 5 compounds of relatively uniform particle shape and size, unlike tobacco used in cigarette manufacture which has been reported to have over 2000 compounds and is present in a myriad of different particles of vastly different sizes and shapes.

Because of the chemical and physical diversity of tobacco, the detection of foreign matter, and particularly small particles of organic foreign matter presents an extremely difficult task. Moreover, cigarette manufacturing speeds have recently increased to greater than 6000–7000 cigarettes per minute. Due to these and other factors, there is presently no commercially available system for detecting organic foreign matter hidden within bulk tobacco.

SUMMARY OF THE INVENTION

In accordance with the invention there is provided an apparatus and method for the detection of foreign matter within a layer of tobacco.

The method and apparatus provided according to this invention are capable of identifying a variety of types of foreign matter including very small pieces of inorganic materials and organic materials such as string and plastics. These and other materials can be identified in accordance with this invention even when hidden beneath the surface in a moving layer of tobacco. The method of the invention is both rapid and accurate so that it can be used on-line in various tobacco product manufacturing processes. Apparatus embodiments of the invention can readily be incorporated into existing tobacco product manufacturing equipment without substantial modification of the equipment.

The method of the invention is accomplished by conveying a layer of tobacco along a predetermined path of travel through an inspection zone. As the layer of tobacco is conveyed through the inspection zone, it is irradiated with NIR radiation comprising a plurality of selected wavelength bands capable of penetrating into tobacco. A plurality of wavelength bands of NIR radiation are separately detected as they exit the layer of tobacco by either reflectance from, or transmittance through the layer. Data representative of the detected NIR radiation is compared with a predetermined reference representative of a plurality of different tobacco samples. The comparison step rapidly and accurately determines whether foreign matter is present within the layer of the tobacco.

In one advantageous embodiment of the invention the predetermined reference used in the comparison step can be data representative of a calculated average NIR spectrum which is the calculated average of a plurality of NIR spectra of samples of tobaccos expected to be present in the tobacco in the inspection zone and which contain no foreign matter.

In another advantageous embodiment, the predetermined reference can be data representative of an average of NIR spectra of tobacco samples expected to be present in the irradiated tobacco but which contain a selected type or types of foreign matter. The different tobaccos expected to be present in the irradiated layer of tobacco can include tobacco cut filler, reconstituted tobaccos, puffed tobaccos, final blends, reconstituted tobacco from stem, and the like.

When NIR radiation is received as reflectance in the inspection zone, the reference data can be representative of NIR spectra at selected wavelength bands preferably within the range of from about 1200 nm to 2400 nm. When NIR transmittance is received in the inspection zone, the reference data can be representative of NIR spectra at wavelength bands preferably within the range of about 800 nm to 1200 nm. In addition, the reference data can be representative of spectra at wavelength bands within both ranges.

The infrared wavelength bands which irradiate the tobacco in the inspection zone, can be narrow, encompassing one or several contiguous wavelengths of NIR light, or they can be relatively broad, encompassing 10–20 or more contiguous wavelengths of NIR radiation. The number of these bands can be relatively small, e.g., 4–6 separate bands, or relatively large, e.g. encompassing all or a substantial portion of the NIR spectrum in discrete, contiguous or non-contiguous bands. A single detector can be used in the receiving means in which case the tobacco is sequentially irradiated with a plurality of wavelength bands; or a plurality of selective detectors can be employed for simultaneous receipt of the plurality of NIR bands, when a broad spectrum light source is used.

The apparatus of the invention includes a conveyor means for conveying a layer of tobacco along a predetermined path of travel through an inspection zone. A tobacco inspection means is associated with the inspection zone and includes an emitter means and a receiving means. The emitter irradiates the tobacco being conveyed through the inspection zone with NIR radiation comprising the plurality of selected wave-length bands capable of penetrating into the tobacco. The receiving means separately receives a plurality of bands of NIR radiation from the irradiated layer of tobacco while it is in the inspection zone. The comparator means then compares data representative of the NIR radiation received by the receiving means with a predetermined reference representative of a plurality of different tobacco samples with or without foreign matter therewithin. These different tobaccos are tobaccos expected to be present in the irradiated layer of tobacco. Advantageously, the comparator means additionally includes analyzing means and storage means. The analyzing means advantageously determines separate values representative of the plurality of wavelengths of NIR radiation received by the receiver. The storage means stores the reference data representative of samples of tobacco with no foreign material and/or with foreign matter. In operation, the comparator means is responsive to the analyzing means for comparing the values determined by the analyzing means with the reference data stored in the storage means.

The method and apparatus of the invention are capable of detecting foreign matter within a layer of tobacco moving through the garniture of a cigarette rod making apparatus so that individual cigarettes can be rejected during the manufacturing process. Inspection of tobacco for foreign matter according to the invention can be both rapid and efficient and can be used in cigarette manufacturing processes in which cigarettes are being produced at a rate of over 6000 cigarettes per minutes using tobacco material which includes a complex matrix of over 2000 compounds and includes numerous particles sizes, shapes and colors.

BRIEF DESCRIPTION OF THE DRAWINGS

In the drawings which form a part of the original disclosure of the invention:

FIG. 2 is a perspective illustration of a cigarette manufacturing apparatus including the detection method and apparatus of the invention;

FIG. 3 is an enlarged perspective view of the inspection zone of FIG. 2;

FIG. 4 is an exploded view of the inspection means shown in FIG. 3 of the invention;

FIG. 5 is a perspective view of another preferred inspection means of the invention which employs NIR transmittance through a conveyed tobacco layer;

DETAILED DESCRIPTION OF THE PREFERRED EMBODIMENTS

In the following detailed description, various preferred embodiments of the invention are described. It is to be understood however, that the invention is not to be limited to its preferred embodiments; to the contrary, the invention includes various alternatives, modifications and equivalents within its spirit and scope as will be apparent to the skilled artisan.

The term "foreign matter" is used herein to include paper and other solid organic materials such as plastics used in wrapping material, natural and synthetic fibers such as those in string, and other matter foreign to tobacco including molds, inorganic solids such as metals or sand, and non-solid material such as oils which may affect the smoking characteristics of a cigarette. The term can also include tobacco material not expected to be present in a particular layer of tobacco being processed into cigarettes.

The term "near infrared (NIR) radiation" is used herein to include radiation at wavelengths within the range of from about 800 nm to about 2400 nm and thus includes radiation at wavelength within the 800 nm to 1200 nm range which sometimes referred to as "near near infrared radiation" or as "shortwave infrared radiation".

Figure 1:
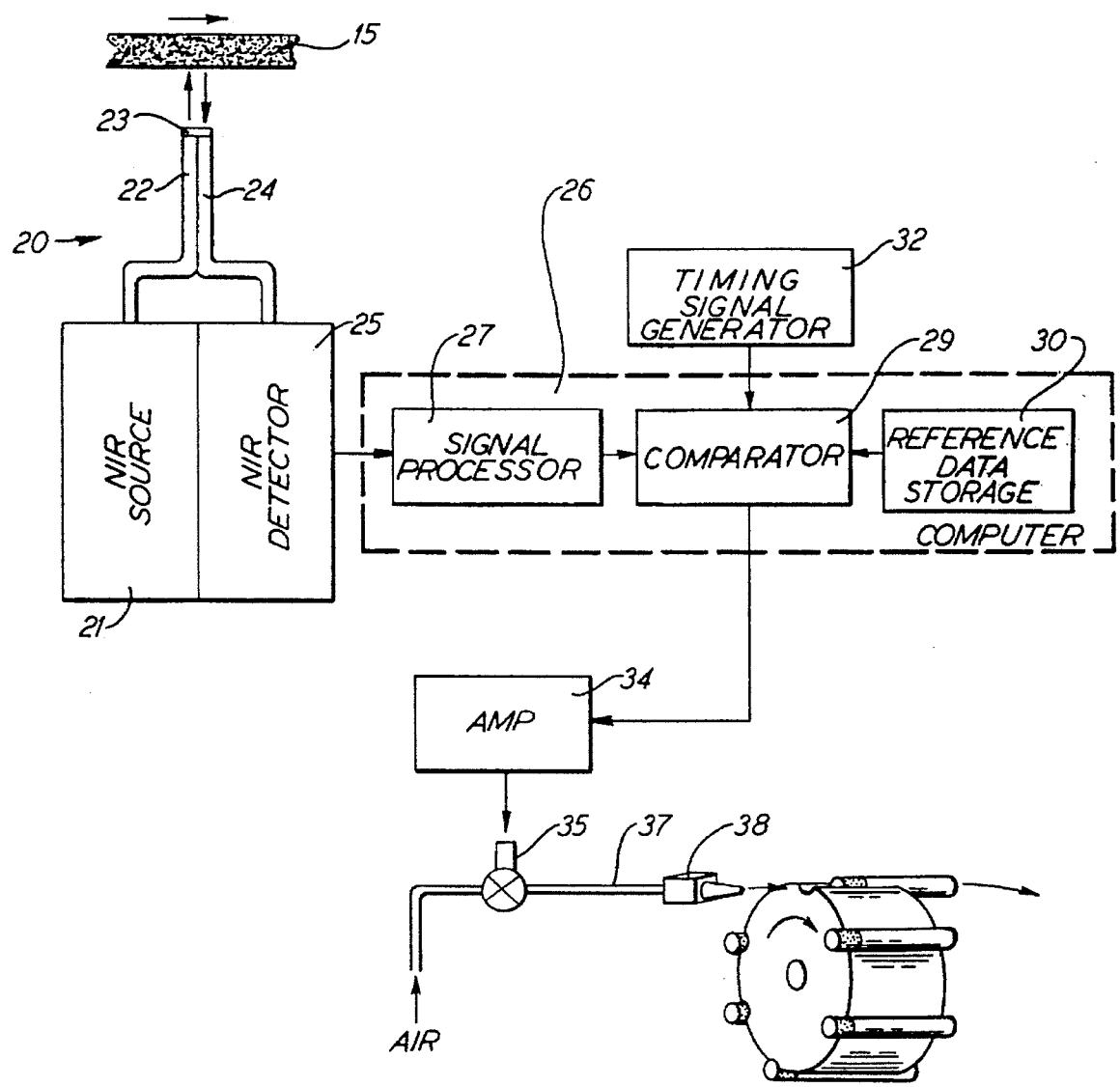
FIG. 1 schematically illustrates the method and apparatus of the invention.

In the process and apparatus of the invention, a layer of tobacco having a thickness ranging from about 0.10 in (0.25 cm) up to about one foot (31 cm) is conveyed through an inspection zone and irradiated with NIR radiation as illustrated schematically in FIG. 1. A layer 15 of tobacco is shown being conveyed past an inspection means 20 in a tobacco inspection zone. This inspection means 20 includes a NIR radiation source 21 for providing NIR radiation to a bundle of optical fibers 22, which in turn emit NIR radiation through a quartz window 23, thereby irradiating the layer 15 of tobacco with NIR radiation. The NIR radiation penetrates into the layer of tobacco 15. The NIR radiation is reflected out of tobacco layer 15 and is received by a second bundle of optical fibers 24 which carries the NIR radiation to the detector 25. The detector then generates an electrical signal representative of the NIR radiation received and sends the signal to a computer 26. The computer 26 preferably is a conventional microcomputer system such as an enhanced IBM/AT computer, ruggedized for use in the factory and including other desirable hardware modifications such as an array processor board or the like to increase the processing rate as necessary depending on the quantity and speed of information fed to the microcomputer, and designed to run the necessary software.

As illustrated in FIG. 1, the NIR source and NIR detector can be provided at a remote location, or the source and/or detector can be positioned within the inspection zone (FIG. 4) and thus emit and/or receive respectively, the NIR radiation directly.

In either case, it is necessary that NIR source generates a plurality of NIR radiation bands either sequentially or simultaneously. Sequential generation of NIR wavelength bands can be accomplished by conventional means such as by employing a rotating filter wheel having 4–20 filters for the sequential generation of 4–20 bands of NIR radiation, each having a band width of e.g. 5–20 nm. Alternative conventional means include a revolving tilting filter wheel or an oscillating holographic grating or other continuous light dispensing optical elements for dispersion of white light into component wavelengths. When the source 21 generates plural wavelengths sequentially, a conventional timing and logic means is associated with the detector 25 for correlation between the sequentially generated wavelength bands and the sequence of reflected NIR radiation received by the detector, as known to the skilled artisan. When the plurality of NIR wavelength bands are generated simultaneously using, e.g., an unfiltered broad band light source, NIR detector 25 can comprise a plurality of detectors which selectively receive different preselected NIR wavelength bands. Selective detectors can be provided by interposing an appropriate filter in front of the detectors. Selective detectors can also be provided in the form of a diode array or a linear detector array in combination with a diffracting and dispersing means such as a stationary holographic grating which selectively diffracts and disperses light of different wavelengths to different locations in the manner of a prism. Thus in the case of either sequential or simultaneous generation of the plural NIR wavelength bands, the detector means 25 separately receives, either sequentially or simultaneously via plural detectors, the NIR radiation exiting tobacco layer 15.

In computer 26, data representative of the received NIR radiation is compared with the predetermined reference representative of a plurality of different tobacco samples to determine whether the irradiated tobacco contains foreign matter. The computer 26 typically includes a signal processor 27 which filters and digitizes the analog signal from detector 25. A comparator 29 compares the signal from processor 27 with reference data from a storage means 30. The comparator is linked to a timing signal generator 32 which generates a signal each time a preselected portion (i.e. the tobacco for one cigarette) of the layer of tobacco passes the receiver The timing signal generator 32 provides the proper time delay corresponding to the time required for the tobacco in the specific cigarette to pass from the inspection zone to the rod and tipping machine and to the location at which it should be ejected if it contains foreign matter. This signal is synchronized and then amplified by amp 34. The signal in amplified form, is applied to the winding of an electromagnetic valve 35. This causes valve 35 to open, permitting pressurized air to pass through conduit 37 and emerge as a blast of air from nozzle 38 which expels a defective cigarette having foreign matter. The tobacco from the rejected cigarette can then be collected, the foreign matter removed and the tobacco reused.

FIG. 2 illustrates one preferred location for the inspection zone of this invention as shown by the location of tobacco inspection means 20 within a commonly available cigarette making machine 40. This apparatus is known and sold commercially by Hauni-Werke Korber and Co., KG, Hamburg, Germany and is described in their U.S. Pat. No. 4,474,190 to Brand, herein incorporated by reference. The machine 40 is designed to manufacture cigarettes at a rate which is in excess of 6000 per minute and is directly coupled with a filter tipping machine (not shown). One such conventional tipping machine is known and also sold commercially as the "MAX 80" by Hauni-Werke Korber and Co., KG, Hamburg, Germany. The cigarette making machine 40 generally includes a preliminary distributor 42 for forming a layer 15 of tobacco and having a pivotal gate 43 wherein tobacco is fed into the machine. A first distributor 44 receives batches of tobacco by way of the gate 43 and a rotary drum-shaped conveyor 45 directs the tobacco to a bulking chute or reservoir 47. A steep angle endless band conveyor 48 draws tobacco particles from the chute 47 to an upright duct 49. The tobacco advances via a carded rotary drum-shaped conveyor 50 which cooperates with a rapidly rotating picker roller (not shown) to form the layer 15 of tobacco on an apron conveyor 52. Tobacco from the apron conveyor 52 is caused to enter a funnel 54 by a curtain of air. The funnel 54 is defined by a carded drum-shaped rotary conveyor 58 and stationary wall member 61. The funnel 54 discharges successive increments of tobacco into an elongated inverted narrow channel 63 defining a predetermined path of travel and providing a means for conveying for the layer 15 of tobacco. The layer grows in the channel 63 and advances lengthwise, i.e. in direction of arrow A.

Referring to FIG. 3, the inverted channel 63 is formed in part by an endless foraminous belt conveyor 65 located in the top of the channel commonly referred to as a "garniture belt". The carding of the conveyor 58 propels the particles of tobacco against the exposed side of the conveyor in the inverted channel 63, and such particles are attracted to the conveyor 65 under the influence of a vacuum source so that the particles form a growing wedge-like stream or layer of tobacco. The layer of tobacco, when fully grown, advances past a conventional trimming or equalizing device 69 serving to remove the surplus or excess of tobacco particles so that the fully grown layer of tobacco is converted into a trimmed or equalized rod-like filler 70.

Referring back to FIG. 2, the filler 70 is thereupon wrapped into a web 71 of cigarette paper or other suitable wrapping material in a portion of its path which is located downstream of the trimming device 69. The web 71 is drawn off an expiring reel 73 which is mounted on the frame adjacent to a fresh reel 73a. A draping mechanism 77 comprising an endless band or belt conveyor eL serves to advance the filler 70 and the web 71 past and through other portions of the mechanism 77. This mechanism is designed to drape the web 71 around the filler so that one marginal portion of the partially draped web extends away from the rodlike filler 70 and one side thereof can be coated with a suitable adhesive (e.g., a wet adhesive or a hot melt) by a conventional paster before the adhesive-coated marginal portion is folded over the other marginal portion to form therewith a seam extending in parallelism with the axis of the resulting continuous cigarette rod 83. The seam is heated or cooled to ensure that the seam can stand stresses which arise when the rod 83 is severed at regular intervals during travel through a cutoff 84 so as to yield a single file of discrete plain cigarette of double unit length.

Referring to FIG. 4, an enlarged and exploded view tobacco inspection means 20 is shown. The inspection means 20 includes a coaxial optical fiber cable 92 which includes an internal cylindrical fiber bundle 22 which emits NIR radiation for irradiating the layer of tobacco with NIR radiation. Advantageously, the internal fiber bundle 22 has a diameter about the same size as the width of inverted channel 63. Annular fiber bundle 24 receives the NIR radiation existing from the layer of tobacco. An optical barrier layer 93 separates the emitting fibers 22 from the receiving fibers 24. The inspection means 2 preferably includes a quartz glass window 23. It will be apparent that other fiber optics or emitter/receiver systems known to those skilled in the art may be used.

As illustrated in FIGS. 3 and 4, one embodiment of the invention utilizes NIR reflectance at wavelengths preferably ranging from about 1200 nm to 2400 nm wherein the layer 15 of tobacco is irradiated and the reflected irradiation is detected or received. Preferably the layer of tobacco has a thickness no greater than about 1 inch (2.5 cm) when NIR reflectance, alone, is used.

FIG. 5 illustrates an embodiment employing NIR transmittance. The NIR radiation at a wavelength ranging from about 800 nm to about 1200 nm is used to penetrate through the layer 15 of tobacco to a parabolic focusing mirror 94 located on the opposite side of the layer, in this case, below the layer. A detector 24 is positioned at the focal point of the mirror 94 to receive the transmitted NIR radiation. An elongated narrow quartz glass window 23 extends transversely across and below moving layer 15 of tobacco 15 to allow transmission of the NIR radiation. As illustrated, this window 23 can be located between the ends of the two conveyors 65.

The use of NIR transmittance employing 800–1200 nm NIR radiation is preferred whenever the layer of tobacco 15 has a thickness greater than about 1 inch (2.5 cm). Transmittance is effective through tobacco layers having a thickness up to about 1 foot (31 cm). Although NIR reflectance is preferably conducted employing NIR radiation in the 1200–2400 nm range and NIR transmittance preferably conducted employing NIR radiation in the 800–1200 nm range, those skilled in the art will recognize that NIR reflectance can also employ NIR radiation in the 800–1200 nm range and that NIR transmittance can also employ NIR radiation in the 1200–2400 nm range. Moreover, the 800–2400 nm range is not viewed as an absolute limitation; radiation at wavelengths adjacent this range can also be advantageously employed.

In addition, NIR transmittance and reflectance can be, and advantageously are used together according to another embodiment of the invention. In this embodiment the apparatus of FIG. 5 includes a second NIR receiver (not shown) located above the layer of tobacco 15, e.g. in housing 96 of the NIR emitter 22. It will be apparent that in this instance, the NIR emitter or emitters will preferably emit a plurality of bands of NIR radiation for each of the ranges 800–1200 nm and 1200–2400 nm.

Use of the apparatus as illustrated in FIG. 5 can be effected in various locations in tobacco processing operations. For example, the apparatus can be used to examine final blends of strip tobacco, prior to casing and/or cutting of the tobacco; or it can be used to examine final blends of cut filler. In addition, any of the various inspection systems of this invention can be used in combination with various conveyor apparatus such as pneumatic conveyors, gravity conveyors, and other known conveying systems.

In one preferred embodiment of the invention, tobacco cut filler exiting a tobacco reclaiming operation is inspected. The reclaiming operation can be one in which tobacco is recovered from defective cigarettes and/or defective packages of cigarettes. In either case, the potential of having solid organic foreign matter, such as packaging materials, filter materials, or the like, in the tobacco is increased. This embodiment can employ NIR reflectance or transmittance or both. When reflectance only, is used, the tobacco is distributed as a thin layer, e.g. about 0.20 inch (1 cm) to about 1.0 inch (2.5 cm) on a moving conveyor belt with the NIR emitter and detector positioned on the same side of, preferably above, the tobacco layer.

Inspection of tobacco on a wide moving conveyor belt, as shown in FIG. 5 or discussed above, is advantageous in that the required rate of analysis is substantially less as compared to the embodiment of the invention illustrated in FIGS. 2–4 since the linear speed of tobacco on a typical wide conveyor belt is much slower than in the garniture of a rod making apparatus. In this regard, the apparatus of FIGS. 2–4 can move a column of tobacco at a rate to produce in excess of 7,000 cigarettes per minute, thus requiring an operating rate in excess of 100 NIR scans and analyses per second to examine tobacco in each cigarette rod. This, in turn, can be accomplished in many various ways, such as, by use of a rotating filter wheel, rotating at a speed in excess of 100 rpm in combination with a microcomputer implemented analysis system. However, when tobacco on a typical wide conveyor is examined, a scan and analysis rate of less than 100 scans and analyses per second can be sufficient.

The detectors used in the various embodiments of the invention are conventional and well-known and can be constructed of various photosensitive materials such as PbS, InGaAs, Si, and the like. As will be apparent to the skilled artisan, detectors can be modified to be selectively sensitive to NIR radiation by interposing an appropriate filter or a dispersing element between the detector and the NIR radiation being transmitted to the detector.

The comparison step of the invention employs as predetermined reference representative of a plurality of different tobacco samples. In one embodiment, the predetermined reference is representative of a plurality of different tobacco samples containing no foreign matter. The tobaccos of this reference are selected to match the tobaccos expected to be present in the layer of tobacco being monitored for foreign matter. For example, separate samples of the following can be prepared from the following:

(1) Reconstituted tobacco;
(2) Puffed tobacco;
(3) Burley tobacco strip;
(4) Flue Cured tobacco strip;
(5) Oriental tobacco strip;
(6) Blends of grades of (3), (4) and (5)
(7) Blends of (3), (4), (5) and (6)
(8) Cut filler samples of (3), (4), (5), (6) and (7)
(9) Final product blend based on the recipe for the particular cigarette;
(10) Reconstituted stem tobacco;
(11) Final cut filler blends;

Separate full or partial NIR analyses are taken for each sample. A statistical analysis program is then used to generate a mean spectrum and standard deviation spectrum representative of all of the samples. Additionally, a weighing function associated with each entry can also be generated to improve selectivity.

Figure 6:
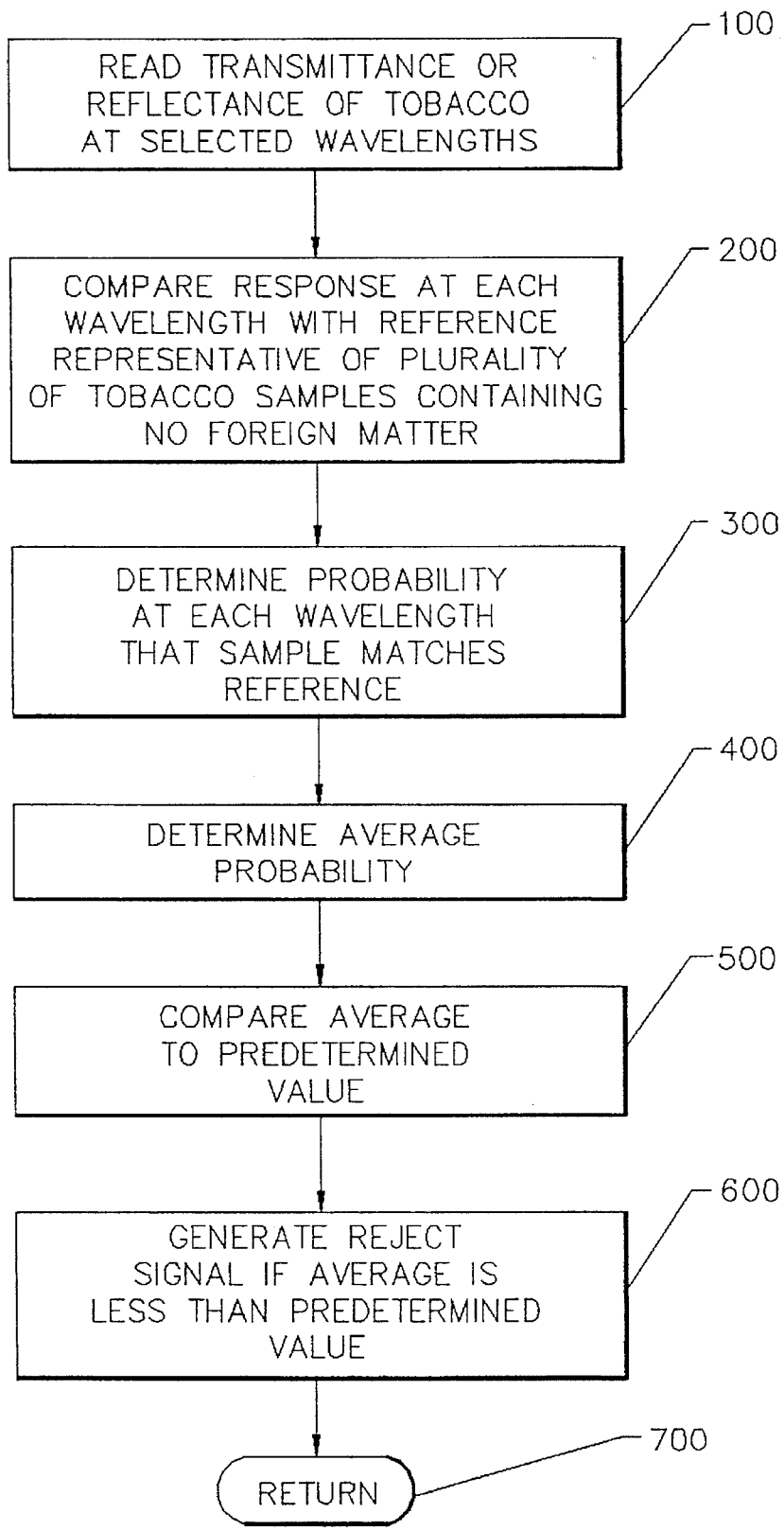
FIG. 6 is a flow chart representation of one preferred method of the present invention.

Now referring to FIG. 6, one embodiment for the method of the present invention is schematically illustrated. The method is advantageously implemented by a control system within the computer 26 which includes software necessary to implement the method of the present invention. Initially, selected wavelengths of NIR radiation are emitted by the emitter 21. A plurality of wavelengths are reflected or transmitted by the layer 15 of tobacco and are separately read into the system in block 100. In block 200, the read NIR radiation is compared to the mean and standard deviation spectra which are representative of a plurality of different tobacco samples containing no foreign matter. In block 300, the system determines the probability at each selected wavelength or wavelength band whether the sample matches the predetermined reference based on the mean and standard deviation reference data according to known statistical analysis techniques. The data then passes to block 400 wherein the mean average probability of the individual probabilities from step 300 is calculated. The result is then compared in block 500 to a predetermined probability value. If the average probability of the sample is less than the predetermined value, block 600 generates a reject signal. Control is then passed to block 700 for return to block 100 wherein the above sequence is repeated with the next portion of the layer of tobacco.

The predetermined reference used in Block 500 is an experimentally determined value which is chosen based primarily on the number, and location of NIR wavelength bands used to irradiate the tobacco being inspected and on the quantity and diversity of spectra used to provide the predetermined reference employed in Block 300. For example, a predetermined reference has been used in the step of Block 300 which was representative of several dozen tobacco samples of the types outlined previously and included mean and standard deviation data for each of the 1200 individual wavelengths ranging from 1200 to 2400 nm. The tobacco being analyzed was irradiated sequentially with the same 1200 individual wavelengths and the reflectance response was separately received for each wavelength. Calculating, as in Block 300, the match probability at each of the 1200 wavelengths, and then averaging the probability as in Block 400, it was found that a value of 50–70%, e.g. 60%, could be used in Block 500. In this regard, it was found that irradiated tobacco with no foreign matter typically had an average match probability (as calculated in Blocks 200, 300 and 400) of 70% or more while irradiated tobacco having a single small particle of paper, string, plastic or the like typically had a total match probability of less than 10%.

Figure 7:
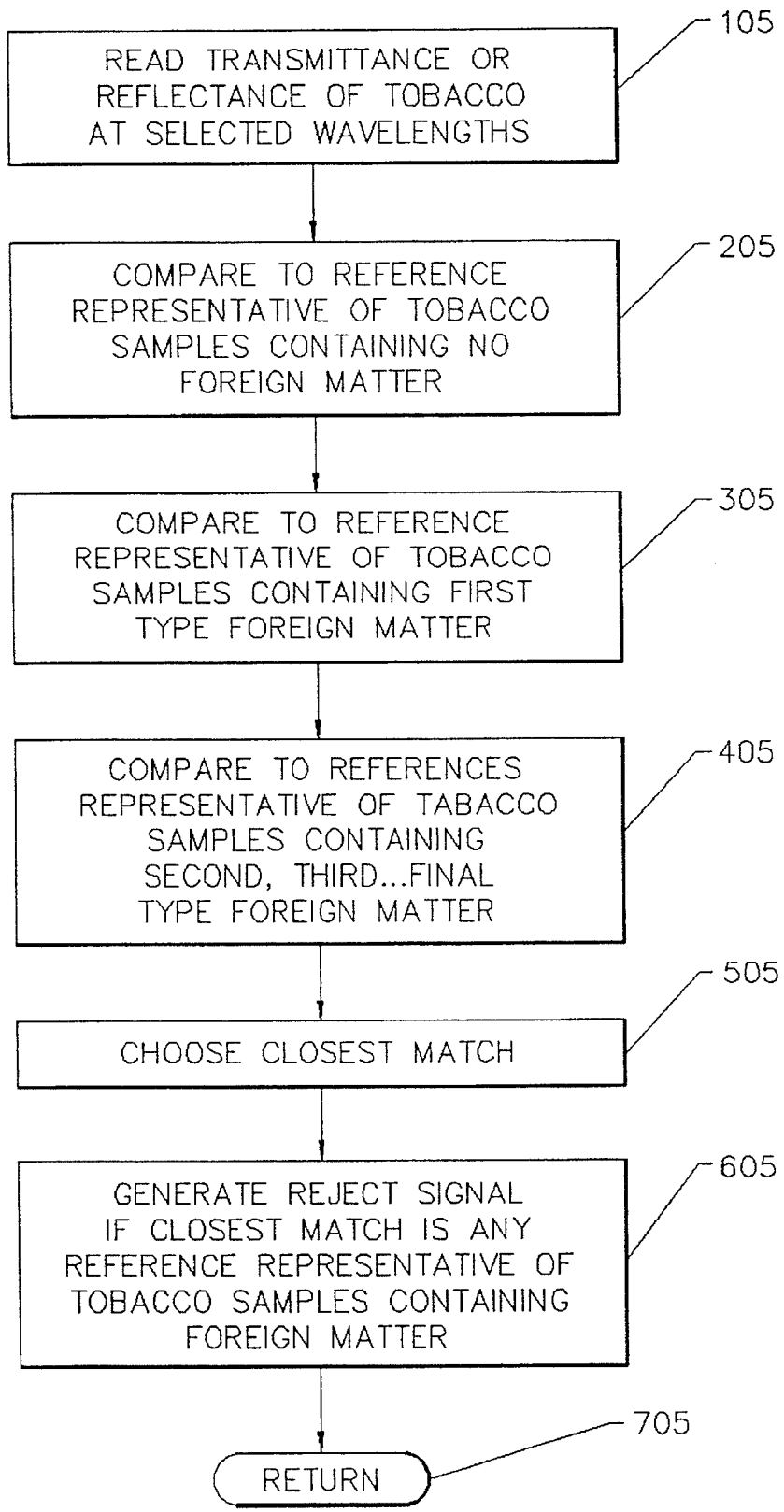
FIG. 7 is a flow chart representative of another preferred method of the present invention.

Referring to FIG. 7, another embodiment of the invention is schematically illustrated which is particularly useful when the tobacco being inspected is scanned for a limited number NIR wavelength band responses. This embodiment employs at least one reference which is representative of plural tobacco samples containing a preselected type of foreign matter in order to simplify the comparison step. Thus this embodiment can be particularly useful in connection with an NIR source employing a rotating filter wheel having, e.g. 7–15 different filters. Selected wave-lengths of NIR radiation are emitted, and a plurality of wavelengths reflected or transmitted by the layer of tobacco are separately read into the system in block 105. In block 205, the read NIR radiation is compared to a predetermined reference comprising data representative of NIR inspection of a plurality of different tobacco samples containing no foreign matter. In block 305, the read radiation is also compared to a predetermined reference representative of a plurality of tobacco samples containing a first preselected foreign matter. This is repeated for any number of references representative of plural tobacco samples containing preselected foreign matter in block 505. For example, the first preselected foreign matter could be string; the second preselected foreign matter, a particular plastic; the third, paper; the fourth, package outer wrap; etc. In block 505, the closest match of average probability is determined, and in block 605 a reject signal is generated if foreign matter is determined to be present. Control is then passed to block 705 for return to block 105 wherein the above sequence is repeated with the next portion of the layer of tobacco.

It will be recognized that analysis according to the FIG. 7 sequence will typically identify fewer types of contaminants as compared to analysis according to the FIG. 6 sequence. However, analysis according to the FIG. 7 sequence can be conducted with substantially less NIR response data than needed for a detailed FIG. 6 type sequential analysis. This in turn allows for a less complex and demanding scan of the tobacco being inspected. For example, as indicated above, in a FIG. 7 type analysis, an NIR source can be used in combination with a rotating filter wheel having, e.g. from about 4 to about 20 filters to provide NIR data on the inspected tobacco at 4–20 different wavelength bands. Alternatively, a single broadband NIR source can be used in combination with, e.g. 4–20 selective detectors to provide the same data. In either case, accuracy of the analysis is accomplished by judicious choice of the NIR wavelength bands used to inspect the tobacco.

The choice of wavelength bands used in a FIG. 7 type analysis can be based on a comparison of known or experimentally determined NIR responses of the specific types of foreign matter in question with known or experimentally determined NIR responses of tobaccos expected to be present in the inspected sample. Specific wavelength bands wherein NIR responses are substantially different between these are then used to inspect the tobacco in the inspection zone.

It is also to be noted that steps shown separately in FIGS. 6 and 7 can be combined. Thus the steps of Blocks 205, 305, 405, and 505 (FIG. 7) could be implemented in a single step analysis by applying to the data obtained by NIR inspection, an equation of the general form $$M = F_1(B_1) + F_2(B_2) \ldots F_n(B_n) + K$$

where M represents the probability that the inspected tobacco best matches one of the tobacco samples containing foreign matter; $B_1, B_2 \ldots B_n$ represent the response of the inspected tobacco to each of the NIR wavelength bands, Band 1, Band 2 through the final Band respectively; $F_1, F_2 \ldots F_n$ are simple or complex functions which, based on known or experimentally determined data, predict the likelihood of whether the NIR response at the particular wavelength band best matches tobacco samples containing foreign matter as compared to tobacco samples containing no foreign matter; and K is an experimentally determined constant.

It will be apparent that the above steps could be embodied in other and varied mathematical analysis techniques known to those skilled in the art. For example, partial least squares can be used to determine sensitive areas of the spectrum for foreign matter in tobaccos and the resultant specific wavelengths identified, monitored, and analyzed according to this technique. Other techniques could include or use artificial intelligence, factor analysis, principal components regression, and the like.

The following example is provided in order to further illustrate various embodiments of the invention but is not to be construed as limiting the scope thereof.

EXAMPLE

Figure 8:
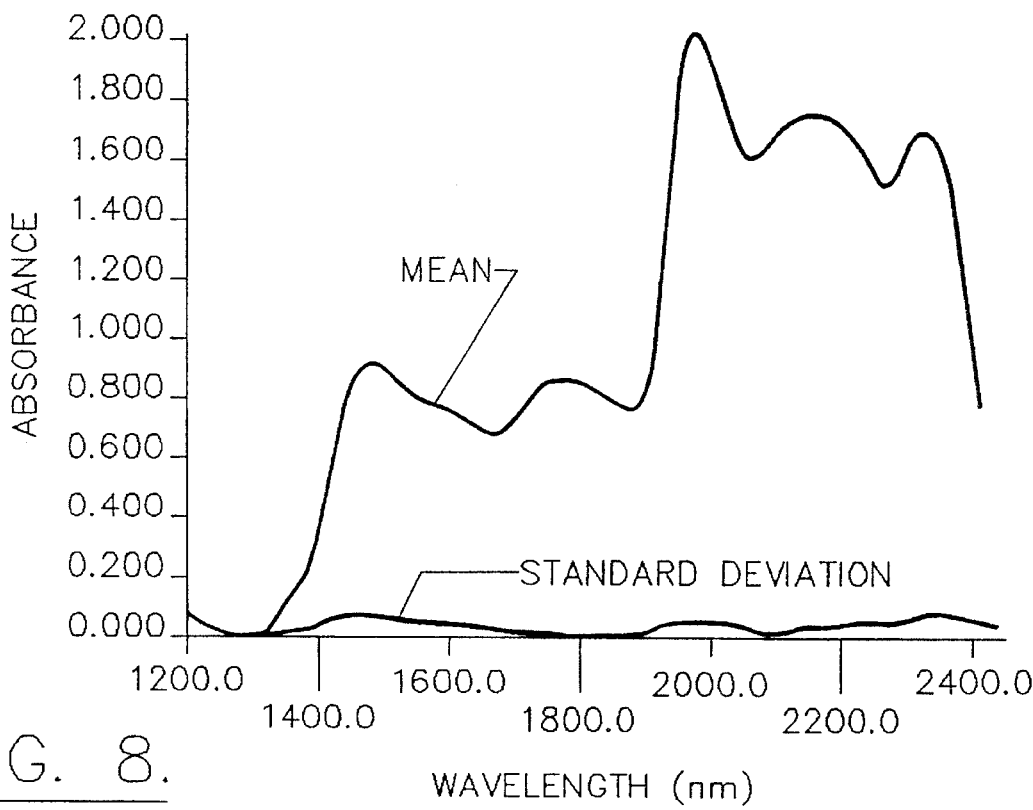
FIGS. 8 and 9 are graphs corresponding to the data obtained in the Example.

Tobacco samples, constituting about 40 different samples, were prepared from single grades and blends of cut filler samples and blends of the following:

(a) Single grades and blends of flue cured cut filler (b) Single grades and blends of Burley cut filler (c) Single grades and blends of Oriental cut filler (d) Partial and final product cut filler blends (e) reconstituted tobacco (f) reconstituted stem tobacco Each sample was irradiated with NIR using a full spectrum scan over the wavelengths ranging from 1200 to 2400 nm and the reflectance response for each sample was stored in the memory of a microcomputer. The scans were taken using an L. T. Industries "QUANTUM 1200" analyzer configured to measure an NIR region. A mean average and standard deviation spectrum for the group of samples was calculated and is shown in FIG. 8.

Figure 9:
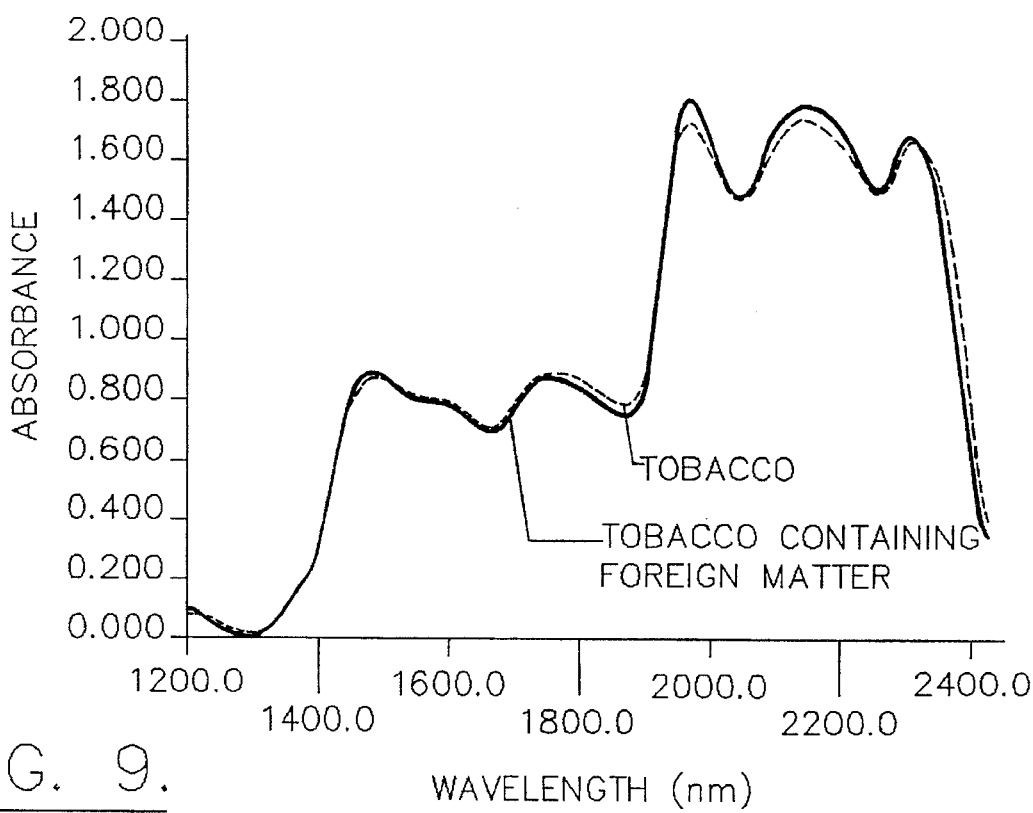

A tobacco sample comprising tobacco cut filler was prepared having a single paper strip 1/32 inch×1/8 inch hidden 15 mm beneath the surface of the sample. The tobacco cut filler was a blend of Flue Cured, Burley, and Oriental tobaccos and also included puffed tobaccos and reconstituted lamina and stem tobaccos. An identical sample without foreign matter was also prepared. These samples were scanned with NIR in the same manner and under the same conditions as in the foregoing to obtain the spectra shown in FIG. 9. For each spectrum, the reflectance response at each wavelength was compared to the corresponding data of FIG. 8 and a probability of match was calculated for each wavelength response. A mean average probability match was then calculated for each spectrum. The match probability for each spectrum was then calculated. The match probability for the sample with no foreign matter was greater than 70%. The match probability for the sample containing paper was less than 5%.

In a like manner, identical tobacco cut filler samples but having strips, 1/32 inch×1/8 inch, of the foreign matter listed below were analyzed to obtain the following results

| Tobacco Sample | Foreign Matter | Match Probability |
| --- | --- | --- |
| 1 | Paper | 3% |
| 2 | EDPM rubber | 0% |
| 3 | Natural rubber | 0% |
| 4 | Polyisoprene/Zinc | 0% |
| 5 | PVC | 4% |
| 6 | Polydimethylsiloxane | 0% |
| 7 | Latex | 0% |
| 8 | Wire Insulation | 0% |

It thus can be seen that the method and apparatus of the present invention provides a means for detecting foreign matter within a layer of tobacco so that tobacco and tobacco products including bulk tobacco and individual cigarettes can be rejected. The method and apparatus can be used in-line and for real time detection even though the cigarettes are being produced at a rate of over 6000 cigarettes per minute using tobacco material which includes a complex matrix of over 2000 components of numerous particles sizes, shapes and colors.

The invention has been described in considerable detail with specific reference to preferred embodiments. However, variations and modifications can be effected within the spirit and scope of the invention as described in the foregoing specification and defined in the appended claims.

That which is claimed is:

1. An apparatus to detect foreign matter within a layer of tobacco, comprising:

conveyor means for conveying a layer of tobacco along a predetermined path of travel through an inspection zone;

emitter means associated with the inspection zone for irradiating the tobacco being conveyed through the inspection one with near infrared radiation the near infrared radiation comprising a plurality of selected wavelength bands within the range from about 800 nm to 2400 nm capable of penetrating into the tobacco;

detector means associated with the inspection zone or separately receiving a plurality of wavelength bands of near infrared radiation from the radiated layer of tobacco while it is in the inspection zone; and comparator means for comparing data representative of the near infrared radiation received by the detector means with a predetermined reference representative of a plurality of different tobacco samples to determine whether the layer of tobacco in the inspection zone contains foreign matter.

2. An apparatus according to claim 1 wherein the predetermined reference representative of a plurality of different tobacco samples is data representative of near infrared reflectance of the tobacco samples at selected wavelength bands within the range comprising from about 1200 nm to 2400 nm.

3. An apparatus according to claim 1 wherein the predetermined reference representative of a plurality of different tobacco samples is data representative of near infrared transmittance through the tobacco samples at selected wavelength bands within the range comprising from bout 800 nm to 1200 nm.

4. An apparatus according to claim 1 wherein the predetermined reference representative of a plurality of different tobacco samples is data representative of near infrared reflectance or transmittance of the samples at selected wavelengths of within the range of from about 800 nm to 2400 nm, and wherein the tobacco samples are samples of tobaccos expected to be present in the irradiated layer of tobacco selected from the group consisting of reconstituted tobacco, puffed tobacco, final blends and reconstituted stem tobacco.

5. An apparatus according to claim 1 wherein the conveyor means for conveying the layer of tobacco is the garniture belt of a cigarette rod making apparatus.

6. An apparatus according to claim 1 wherein the layer of tobacco is bulk tobacco in strip form having a thickness of up to about one foot.

7. An apparatus according to claim 1 wherein the solid foreign matter is a solid organic material.

8. An apparatus according to claim 1 wherein the layer of tobacco comprises cut filler tobacco from a reclaiming process.

9. An apparatus to detect foreign matter in a layer of tobacco, comprising:

tobacco inspection means comprising an emitter means for irradiating the layer of tobacco with near infrared radiation comprising a plurality of selected wavelengths within the range from about 800 nm to 2400 nm capable of penetrating into the layer of tobacco and a receiver means for receiving near infrared radiation from the irradiated layer of tobacco;

analyzing means responsive to the tobacco inspection means for determining a plurality of separate values representative of a plurality of preselected wavelength bands of near infrared radiation received by the receiver means;

storage means for storing reference data representative of an average of a plurality of different tobacco samples containing no foreign matter, the tobacco samples comprising tobaccos expected to be present in the irradiated layer of tobacco; and comparator means responsive to the analyzing means for comparing the values determined by the analyzing means with the reference data stored in the storage means to determine whether the layer of tobacco contains foreign matter.

10. An apparatus according to claim 9 wherein the predetermined reference representative of a plurality of different tobacco samples is data representative of near infrared reflectance of the samples comprising selected wavelength bands within the range of from about 1200 nm to 2400 nm.

11. An apparatus according to claim 9 wherein the predetermined reference representative of a plurality of different tobacco samples is data representative of near infrared transmittance through the samples comprising selected wavelengths within the range from about 800 nm to 1200 nm.

12. An apparatus according to claim 9 wherein the emitter means and the receiver means are positioned on the same side of the tobacco layer.

13. An apparatus according to claim 9 wherein the layer of tobacco is bulk tobacco in strip form having a thickness of up to about one foot.

14. An apparatus according to claim 9 wherein the foreign matter is a solid organic material.

15. An apparatus to detect solid foreign matter in tobacco, comprising:

tobacco inspection means comprising an emitter means for irradiating tobacco with near infrared radiation comprising a plurality of selected wavelength bands within the range from about 800 nm to 2400 nm capable of penetrating into the layer of tobacco and a receiver means for receiving near infrared radiation from the layer of tobacco;

analyzing means responsive to the tobacco inspection means for determining a plurality of separate values representative of a plurality of preselected wavelength bands of near infrared radiation received by the receiver means;

storage means for storing reference data representative of a plurality of different tobacco samples; and comparator means responsive to the analyzing means for comparing the values determined by the analyzing means with the reference data stored in the storage means to determine whether the tobacco contains foreign matter.

16. An apparatus according to claim 15 wherein the reference data stored in the storage means is data representative of near infrared reflectance or transmittance of the plurality of tobacco samples at a plurality of wavelength bands within the range of between about 800 nm and 2400 nm.

17. An apparatus according to claim 16 wherein the data stored in the storage means comprises data representative of a plurality of tobacco samples containing foreign matter.

18. An apparatus according to claim 16 wherein the data stored in the storage means comprises data representative of a plurality of tobacco samples containing no foreign matter.

19. An apparatus according to claim 18 wherein the data stored in the storage means comprises data representative of the average of a plurality of full or partial NIR spectra of a plurality of tobacco samples containing no foreign matter.

20. An apparatus according to claim 16 wherein the data stored in the storage means comprises data representative of the average of a plurality of full or partial NIR spectra of a plurality of tobacco samples containing a first predetermined type of foreign matter.

21. The apparatus of claim 20 wherein the data stored in the storage means additionally comprises data representative of the average of a plurality of full or partial NIR spectra of a plurality of tobacco samples containing a second predetermined type of foreign matter.

22. An apparatus for detecting foreign matter in tobacco comprising:

distributor means for forming a layer of tobacco; conveyor means for conveying the layer of tobacco along a predetermined path of travel from the distributor means rapidly through an inspection zone;

emitter means positioned adjacent the conveying means for irradiating the layer of tobacco being conveyed through the inspection zone with near infrared radiation comprising a plurality of preselected wavelengths in the range of about 1200 nm to about 2400 nm;

receiving means positioned adjacent the conveyor means and being located to receive near infrared radiation reflected from the irradiated layer of tobacco being conveyed through the inspection zone;

comparator means for comparing the near infrared radiation received by the receiving means with a predetermined reference representative of a plurality of selected tobacco samples to determine whether the layer of tobacco in the inspection zone contains foreign matter within the layer of tobacco; and reject means responsive to the comparator means for rejecting tobacco containing foreign matter.

23. The apparatus of claim 22 additionally comprising smoking article forming means positioned between the conveyor means and the reject means.

24. An apparatus according to claim 22 wherein the comparator means additionally includes analyzing means responsive to the receiving means for separately determining values representative of a plurality of preselected wavelengths of infrared radiation received by the receiver means and storage means for storing reference data representative of tobacco containing foreign matter; wherein the comparator means is responsive to the analyzing means for comparing the values determined by said analyzing means with the reference data stored in the storage means.

25. An apparatus according to claim 22 wherein the comparator means includes analyzing means responsive to the tobacco inspection means for separately determining values representative of a plurality of preselected wavelengths of near infrared radiation received by the receiver means and the storage means for storing reference data comprises data representative of an average of a plurality of different tobacco samples containing no foreign matter and comprising tobaccos expected to be present in the irradiated layer of tobacco.

26. An apparatus according to claim 22 wherein the predetermined reference representative of a plurality of selected tobacco samples is data representative of near infrared reflectance of the tobacco samples at selected wavelengths within the range of from about 1200 nm to 2400 nm.

27. An apparatus according to claim 22 wherein the predetermined reference representative of a plurality of selected tobacco samples is data representative of near infrared transmittance of the tobacco samples at selected wavelengths within the range from about 800 nm to 1200 nm.

28. The apparatus of any of claims 22 and 26–29 additionally comprising a tobacco reclaiming means for reclaiming tobacco from cigarettes or packages of cigarettes, the tobacco reclaiming means being operatively associated with the distributor means and the layer of tobacco being tobacco from the tobacco reclaiming means.

29. An apparatus according to claim 22 wherein the layer of tobacco is bulk tobacco in strip form having a thickness of up to about one foot.

30. An apparatus according to claim 22 wherein the foreign matter is a solid organic material.

31. An apparatus for manufacturing smoking articles comprising:

distributor means for forming a layer of tobacco in an inverted channel;

conveyor means in the top of the inverted channel for conveying the layer of tobacco along the inverted channel;

trimming means positioned adjacent the inverted channel for trimming excess particles off the layer of tobacco being conveyed along the inverted channel;

tobacco inspection means positioned downstream of the trimming means and comprising an emitter means positioned below the inverted channel for irradiating the tobacco being conveyed along the inverted channel and a receiver means positioned below the inverted channel for receiving radiation from the tobacco being conveyed along the inverted channel;

tobacco rod forming means for forming a tobacco rod from the layer of tobacco being conveyed along the inverted channel;

smoking article forming means for forming smoking articles from the tobacco rod; and reject means responsive to the tobacco inspection means for rejecting smoking articles containing foreign matter.

32. An apparatus according to claim 31 wherein the emitter means positioned below the inverted channel for irradiating the layer of tobacco being conveyed along the inverted channel irradiates the tobacco with near infrared radiation comprising a plurality of preselected wavelengths in the range of 1200 nm to about 2400 nm; and wherein the apparatus additionally includes comparator means for comparing the radiation received by the receiving means with a predetermined reference representative of a plurality of selected tobacco samples to determine whether the layer of tobacco being conveyed along the inverted channel contains foreign matter.

33. An apparatus according to claim 32 wherein the comparator means additionally includes analyzing means responsive to the receiving means for separately determining values representative of a plurality of preselected wavelengths of infrared radiation received by the receiver means and storage means for storing reference data representative of tobacco containing foreign matter.

34. An apparatus according to claim 32 wherein the comparator means includes analyzing means responsive to the receiving means for separately determining values representative of a plurality of preselected wavelengths of near infrared radiation received by the receiver means and storage means for storing reference data representative of an average of a plurality of different tobaccos containing no foreign matter wherein the comparator means is responsive to the analyzing means for comparing the values determined by the analyzing means with the reference data stored in the storage means.

35. An apparatus according to claim 32 wherein the predetermined reference representative of a plurality of selected tobacco samples is data representative of near infrared reflectance of the tobacco samples at selected wavelengths within the range of from about 1200 nm to 2400 nm, and wherein the tobacco samples are representative of different tobaccos expected to be present in the irradiated layer of tobacco.

36. A method for detecting foreign matter within a layer of tobacco, comprising the steps of:

conveying a layer of tobacco along a predetermined path of travel through an inspection zone;

irradiating the layer of tobacco as it is conveyed through the inspection zone with near infrared radiation comprising a plurality of selected wavelength bands within the range from about 800 nm to 2400 nm capable of penetrating into the layer of tobacco and separately receiving a plurality of near infrared radiation bands exiting the tobacco; and comparing the infrared radiation received from the tobacco in the inspection zone with a predetermined reference representative of a plurality of different tobacco samples containing no foreign matter to determine whether the irradiated layer of tobacco contains foreign matter, the plurality of different tobacco samples comprising tobaccos expected to be present in the irradiated layer of tobacco.

37. A method according to claim 36 wherein the predetermined reference representative of a plurality of different tobacco samples is data representative of near infrared reflectance of the tobacco samples at selected wavelength bands within the range of from about 1200 nm to 2400 nm.

38. A method according to claim 36 wherein the predetermined reference representative of a plurality of different tobacco samples is data representative of near infrared transmittance of the tobacco samples at selected wavelength bands within the range from about 800 nm to 1200 nm.

39. A method according to claim 36 wherein the predetermined reference representative of a plurality of different tobacco samples is data representative of near infrared reflectance and transmittance of the tobacco samples at selected wavelengths of within the range of from about 800 nm to 2400 nm.

40. A method for detecting foreign matter in a layer of tobacco, comprising the steps of:

irradiating the layer of tobacco with near infrared radiation comprising a plurality of selected wavelengths within the range from about 800 nm to 2400 nm capable of penetrating into the layer of tobacco;

receiving near infrared radiation from the irradiated layer of tobacco;

analyzing the received near infrared radiation to determine a plurality of separate values representative of a plurality of preselected wavelength bands of near infrared radiation; and comparing the values determined by analyzing the received near infrared radiation with stored reference data representative of an average of a plurality of different tobaccos containing foreign matter, the different tobaccos comprising tobaccos expected to be present in the irradiated layer of tobacco.

41. A method according to claim 40 wherein the predetermined reference representative of a plurality of different tobacco samples is data representative of near infrared reflectance of the tobacco samples at selected wavelengths within the range of from about 1200 nm to 2400 nm.

42. A method according to claim 40 wherein the predetermined reference representative of a plurality of different tobacco samples is data representative of near infrared transmittance of the tobacco samples at selected wavelengths within the range from about 800 nm to 1200 nm.

43. A method according to claim 40 wherein the predetermined reference representative of a plurality of different tobacco samples is data representative of near infrared reflectance and transmittance of the tobacco samples at selected wavelengths of within the range of from about 800 nm to 2400 nm.

44. A method for forming smoking articles devoid of foreign matter comprising:

forming a layer of tobacco;

conveying a layer of tobacco along a predetermined path of travel through an inspection zone;

irradiating the layer of tobacco as it is conveyed through the inspection zone with near infrared radiation comprising a plurality of selected wavelengths within the range from about 800 nm to 2400 nm capable of penetrating into the layer of tobacco and separately receiving a plurality of near infrared radiation bands exiting the tobacco; and comparing infrared radiation received from the tobacco in the inspection zone with a predetermined reference representative of a plurality of different tobaccos contain no foreign matter to determine whether the layer of tobacco contains foreign matter;

forming a smoking article from the layer of tobacco; and rejecting smoking articles containing foreign matter in response to the comparing step.

45. A method according to claim 44 wherein the predetermined reference representative of a plurality of different tobacco samples is data representative of near infrared reflectance of the tobacco samples at selected wavelengths within the range of from about 1200 to 2400 nm.

46. A method according to claim 44 wherein the predetermined reference representative of a plurality of different tobacco samples is data representative of near infrared transmittance of the tobacco samples at selected wavelengths within the range from about 800 nm to 1200 nm.

47. A method according to claim 44 wherein the predetermined reference representative of a plurality of different tobacco samples is data representative of near infrared reflectance and transmittance of the tobacco samples at selected wavelengths within the range of from about 800 nm to 2400 nm.

* * * * *